United States Patent
Woo et al.

(10) Patent No.: US 6,303,200 B1
(45) Date of Patent: Oct. 16, 2001

(54) LOW MODULUS AND AUTOCLAVABLE MONOLAYER MEDICAL TUBING

(75) Inventors: Lecon Woo, Libertyville; Michael T. K. Ling, Vernon Hills, both of IL (US); Patrick Balteau, Bothey (BE); Ying-Cheng Lo, Green Oaks; Ketan Shah, Gurnee, both of IL (US); Hénaut J. Eric, Arquennes (BE); Yuan-pang Samuel Ding, Vernon Hills, IL (US); Stanley Westphal; Robert Wojnarowski, both of Zion, IL (US)

(73) Assignee: Baxter International Inc., Deerfield, IL (US)

( * ) Notice: Subject to any disclaimer, the term of this patent is extended or adjusted under 35 U.S.C. 154(b) by 0 days.

(21) Appl. No.: 09/014,217

(22) Filed: Jan. 27, 1998

(51) Int. Cl.$^7$ ............................ B29D 23/00; A61M 5/00; C08L 9/00; C08L 53/00
(52) U.S. Cl. ................... 428/36.9; 604/264; 604/403; 525/95; 525/98
(58) Field of Search .................... 428/36.9, 36.92, 428/35.7; 604/403, 408, 264; 525/95, 98

(56) References Cited

U.S. PATENT DOCUMENTS

| | | | |
|---|---|---|---|
| 3,865,776 | * 2/1975 | Gergen | 524/505 |
| 4,198,983 | * 4/1980 | Becker et al. | 604/266 |
| 4,479,989 | * 10/1984 | Mahal | 428/35.5 |
| 4,511,354 | 4/1985 | Sterling | 604/98 |
| 4,613,640 | * 9/1986 | Deisler et al. | 524/264 |
| 4,616,064 | 10/1986 | Zukosky et al. | 525/92 B |
| 4,619,642 | 10/1986 | Spencer | 604/29 |
| 4,698,059 | * 10/1987 | Johnson | 604/270 |
| 4,814,375 | * 3/1989 | Esposito | 524/505 |
| 5,777,031 | * 7/1998 | Djiauw et al. | 525/98 |

* cited by examiner

*Primary Examiner*—Rena L. Dye
(74) *Attorney, Agent, or Firm*—Charles R. Mattenson; Paula J. Kelly; Joseph A. Fuchs

(57) ABSTRACT

A steam sterilizable monolayer medical tubing comprising a blend of a melt strength enhancing agent of a homopolymer or copolymer of polypropylene having free-end long chain branches of propylene units, a melt flow index of greater than 10 and in an amount of 1–10% by weight and a second component selected from the group of (i) a selectively hydrogenated block copolymer of a vinyl aromatic hydrocarbon and a conjugated diene and (ii) a selectively hydrogenated block copolymer of a vinyl aromatic hydrocarbon and a conjugated diene to which has been grafted, an alpha, beta-olenfically unsaturated monocarboxylic or dicarboxylic acid reagent.

9 Claims, 1 Drawing Sheet

LOW MODULUS AND AUTOCLAVABLE MONOLAYER MEDICAL TUBING

TECHNICAL FIELD

This invention relates to medical tubing compositions and more particularly to an autoclavable monolayer tubing which is suitable for high speed manufacturing and bonding to polymers such as polycarbonates, polyesters, and polypropylenes.

BACKGROUND ART

In the medical field, where beneficial agents are collected, processed and stored in containers, transported and ultimately delivered through tubes by infusion to patients, there has been a recent trend toward developing materials useful for fabricating such containers and tubing without the disadvantages of currently used materials such as polyvinyl chloride (PVC). These new medical tubing materials must have a unique combination of properties, so that the tubing can be used in fluid administration sets and with medical infusion pumps. These materials must have good bonding properties, sufficient yield strength and flexibility, be environmentally friendly and compatible with medical solutions, and exhibit little post-autoclave coil set. In addition, to be commercially viable, the tubing must be extrudable at high speeds, greater than 50 ft/min.

It is a requirement that the tubing be environmentally compatible as a great deal of medical tubing is disposed of in landfills and through incineration. For tubing disposed of in landfills, it is desirable to use as little material as possible to fabricate the tubing. To this end, it is desirable to use a material which is thermoplastically recyclable so that scrap generated during manufacturing may be refabricated into other useful articles.

For tubing that is disposed of by incineration, it is necessary to use a material that does not generate or minimizes the formation of by-products such as inorganic acids which may be environmentally harmful, irritating, and corrosive. For example, polyvinyl chloride may generate objectionable amounts of hydrogen chloride (or hydrochloric acid when contacted with water) upon incineration, causing corrosion of the incinerator and possibly presenting other environmental concerns.

To be compatible with medical solutions, it is desirable that the tubing material be free from or have a minimal content of low molecular weight additives such as plasticizers, stabilizers, and the like. These components could be extracted by the therapeutic solutions that come into contact with the material. The additives may react with the therapeutic agents or otherwise render the solution ineffective. This is especially troublesome in bio-tech drug formulations where the concentration of the drug is measured in parts per million (ppm), rather than in weight or volume percentages. Even minuscule losses of the bio-tech drug can render the formulation unusable. Because bio-tech formulations can cost several thousands of dollars per dose, it is imperative that the dosage not be changed.

Bonding properties are important because medical tubings are often connected to a port of an I.V. container or a continuous ambulatory peritoneal dialysis (CAPD) container or other junction components within a fluid administration set. Therefore, it is necessary that the tubing be capable of attaching to polymers such as polyesters, polycarbonates, and polyolefins which are commonly used to fabricate such junctions.

Autoclavable medical tubing must be flexible. The majority of autoclavable medical tubings are produced from polyvinyl chloride. Because polyvinyl chloride by itself is a rigid polymer, low molecular weight components known as plasticizers must be added to render polyvinyl chloride flexible. However, these plasticizers may be extracted out of the tubing by the fluid. For this reason, and because of the difficulties encountered in incinerating polyvinyl chloride, there is a need to replace polyvinyl chloride medical tubing.

The tubing must also exhibit very little coil set and a small spring constant after autoclave. Coil set is a phenomenon where the tubing retains a helical shape after it has been unwound from a spindle or the like. Coil set is a problem because it causes the tubing to be physically shortened. In addition, a tubing exhibiting coil set possesses a degree of potential energy when it is straightened for use. When the tubing is used to connect an I.V. or a CAPD container to a patient, the potential energy creates an undesirable pulling force on the exit site of the patient. The pulling force can cause pain and discomfort to the patient, and eventually, infection may occur.

Non-polyvinyl chloride tubings are available; however, these tubings are not suitable for applications where flexibility and sealing rely on the elastic properties of the tubings. For instance, oil-modified styrene-ethylene-butene-styrene (SEBS), such as Kraton G2705 manufactured by Shell Chemical Company, has the necessary flexibility, but tubings produced from Kraton G2705 cannot be manufactured at a high rate due to extremely poor melt strength caused by phase separation at the extrusion temperature. This phase separation causes the Kraton G2705 tubings to melt fracture. Thus, as the tubing produced from Kraton G2705 is extruded at commercial speeds, it breaks into pieces.

U.S. Pat. No. 4,041,103 (Davison et al.) and U.S. Pat. No. 4,429,076 (Saito et al.) disclose non-polyvinyl chloride polymeric blends of a polyamide and SEBS. However, the polymeric materials of these patents generally fail to provide the physical properties required for medical tubings. For example, Davison et al. discloses illustrative blends of various combinations of block copolymers, with nylons, and in some cases other components such as polypropylene and ethylene vinyl acetate copolymers. The majority of the blends of Davison et al. specify using nylon 6. The polymeric materials of Davison et al. are more suited to end uses which are subjected to high temperature oxidation environments such as automotive under-the-hood applications or electrical power cable applications. (Col. 6, line 67 to col. 7, line 3).

Saito et al. discloses a polymeric material having 1% to 99% SEBS and the balance being a polyamide. The polymeric compositions of Saito et al. are typically injection or blow molded into automobile parts, electrical parts, mechanical parts, medical equipment, packaging materials, and building materials. (Column 16, lines 46–50).

Others have used SEBS in tubing and films as a component in a blend. U.S. Pat. No. 4,803,102 (Raniere et al.) and U.S. Pat. No. 5,356,709 (Woo et al.) disclose multilayered structures where SEBS blends are used as a layer within the multilayered structures.

For instance, Raniere et al. discloses a multi-layer packaging film. The outer or heat sealing layer being produced from a mixture of not less than 10% by weight polypropylene and up to 90% by weight SEBS. Similarly, Woo et al. discloses a multi-layered tubing. The outer layer of the tubing is produced from a blend of 40 to 99% by weight polypropylene and 1 to 60% by weight SEBS.

Neither Raniere et al. nor Woo et al. disclose using a polypropylene and SEBS blend as a monolayer tubing.

Further, neither Raniere et al. nor Woo et al. disclose using a high melt strength polypropylene in its polypropylene and SEBS layer.

The present invention is provided to solve these and other problems.

DISCLOSURE OF INVENTION

The present invention provides a polyvinyl chloride-free monolayer medical tubing. The medical tubing of the present invention exhibits many of the characteristics which are required by the medical industry including flexibility comparable to plasticized polyvinyl chloride, minimal dust adherence, low coil set, and the ability to seal to other components.

The medical tubing disclosed herein is capable of withstanding the temperatures and pressures reached during a standard autoclave process without significant thermal degradation. The polymeric material comprises a blend of a melt strength enhancing agent of a polyolefin and preferably a homopolymer or a copolymer of a polypropylene having a melt flow index greater than 10 grams/10 min. and a second component preferably a styrene and hydrocarbon copolymer. The second component is more preferably selected from a group consisting of a selectively hydrogenated block copolymer of a vinyl aromatic hydrocarbon and a conjugated diene, and a selectively hydrogenated block copolymer of a vinyl aromatic hydrocarbon and a conjugated diene to which has been grafted an alpha, beta-olenfically unsaturated monocarboxylic or dicarboxylic acid reagent. This second component is preferably a hydrogenated styrene-butadiene-styrene (SBS) resulting in styrene-ethylene-butene-styrene (SEBS). Most preferred is an oil-modified SEBS such as the commercially available KRATON G2705 from the Shell Chemical Company.

Other advantages and aspects of the present invention will become apparent upon reading the following description of the drawings and detailed description of the invention.

BEST MODE FOR CARRYING OUT THE INVENTION

Figure 1:
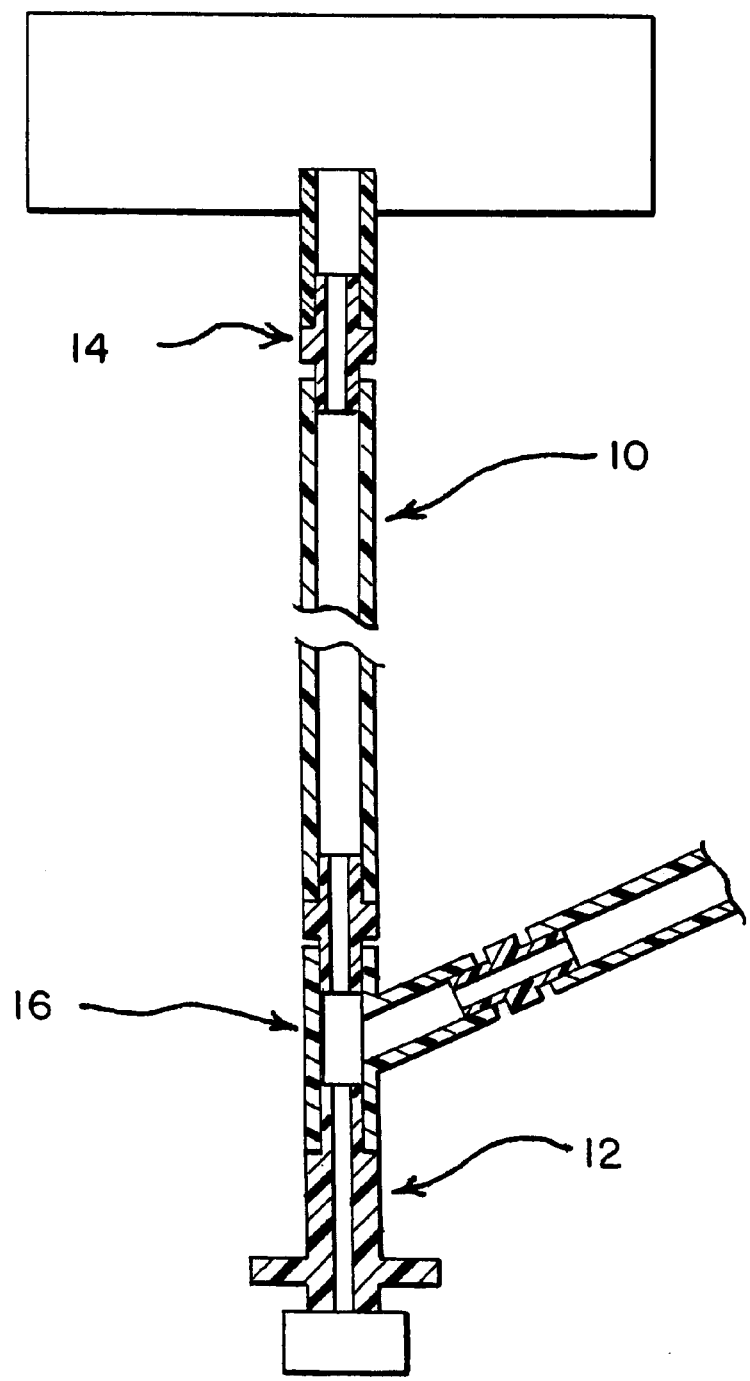
FIG. 1 shows tubing of the present invention connected to various rigid housings.

While the invention is susceptible of embodiment in many different forms, there is shown in the drawings and will herein be described in detail preferred embodiments of the invention with the understanding that the present disclosure is to be considered as an exemplification of the principles of the invention and is not intended to limit the broad aspect of the invention to the embodiments illustrated.

The present invention comprises an autoclavable monolayer medical tubing which is suitable for high speed extruding (at least 50 ft/min.) and bonding to components made from polycarbonates, polyesters, polyolefins, blends of polyolefins, polypropylenes, and other polymers and a method for using the tubing. The medical tubing is produced from a blend of a melt strength enhancing agent in an amount of 1% to 10by weight and a styrene and hydrocarbon copolymer in an amount of 90% to 99% by weight.

The melt strength enhancing agent is a polyolefin and more preferably is a homopolymer or copolymer of polypropylene having a melt flow index within the range of 10 grams/10 min. to 800 grams/10 min., more preferably 30 grams/10 min. to 200 grams/10 min, or any range or combination of ranges therein. This component is a homopolymer or copolymer of polypropylene having a high melt strength characteristic. Methods of preparing polypropylenes which exhibit a high melt strength characteristic have been described in U.S. Pat. Nos. 4,916,198; 5,047,485; and 5,605,936 which are hereby incorporated by reference and part hereof. One such method includes irradiating a linear propylene polymer in an environment in which the active oxygen concentration is about 15% by volume with high energy ionization energy radiation at a dose of 1 to $10^4$ megarads per minute for a period of time sufficient for a substantial amount of chain scission of the linear propylene polymer to occur but insufficient to cause the material to become gelatinous. The irradiation results in chain scission. The subsequent recombination of chain fragments results in the formation of new chains, as well as joining chain fragments to chains to form branches. This further results in the desired free-end long chain branched, high molecular weight, non-linear, propylene polymer material. Radiation is maintained until a significant amount of long chain branches form. The material is then treated to deactivate substantially all the free radicals present in the irradiated material.

Copolymers of polypropylene preferably contain a suitable comonomer component within the range of 1 to 15% by weight. Suitable comonomers include those monomers selected from the group consisting of alpha-olefins having 1 to 10 carbon atoms. Useful copolymers include the random copolymers of propylene with ethylene where the ethylene content is in an amount within the range of 1 to 6%, and more preferably 2 to 4%, or any range or combination of ranges therein. In addition, the propylene alpha-olefin random copolymers (PPE) are especially useful. Preferably, the alpha-olefin random copolymers will have a narrow molecular weight range. This melt strength enhancing component increases the strength of the blend at melt temperatures and allows the blend to be extruded at commercial speeds.

Furthermore, in addition to having poor melt strength, dust adheres to the surface of finished products made from the styrene and hydrocarbon copolymers. However, when alloyed with or modified by a high melt strength and high melt flow homopolymer or copolymer of polypropylene, this deficiency is also eliminated.

The styrene and hydrocarbon copolymer is preferably selected from the group of a selectively hydrogenated block copolymer of a vinyl aromatic hydrocarbon and a conjugated diene and a selectively hydrogenated block copolymer of a vinyl aromatic hydrocarbon and a conjugated diene to which has been grafted, an alpha, beta-olenfically unsaturated monocarboxylic or dicarboxylic acid reagent.

The selectively hydrogenated block copolymers can be chosen from diblock, triblock, multiblock, polyblock, starblock, or graftblock copolymers. These block copolymers can be prepared by any of the well-known block polymerization or copolymerization procedures such as those disclosed in U.S. Pat. Nos. 3,251,905; 3,390,207; and 4,219,627 which are hereby incorporated by reference. The vinyl aromatic hydrocarbons used to prepare the copolymer include styrene, and the various substituted styrenes including o-methylstyrene, p-methylstyrene, p-tert-butylstyrene, 1,3-dimethylstyrene, alpha-methylstyrene, beta-methylstyrene, p-isopropylstyrene, 2,3-dimethylstyrene, o-chlorostyrene, p-chlorostyrene, o-bromostyrene, and 2-chloro-4-methylstyrene. The conjugated dienes include those containing preferably 2 to 30 carbon atoms. Conjugated dienes of this type can be selected from the group comprising 1,3-butadiene, 2-methyl-1,3-butadiene, 2,3-dimethyl-1,3-butadiene, chloroprene, 1,3-pentadiene, and 1,3-hexadiene.

The styrene and hydrocarbon copolymer may comprise a block copolymer of styrene-isoprene-styrene. A hydrogenated styrene-butadiene-styrene (SBS) resulting in styrene-ethylene-butene-styrene (SEBS) is more preferred. Most preferred is an oil-modified SEES copolymer. The amount of oil added to the SEES is preferably within the range of 5% to 40% by weight of a mineral oil, polybutene oil, or the like and most preferably 30% by weight of a mineral oil, polybutene oil or the like, or any range or combination of ranges therein. One such oil-modified SEBS copolymer is the commercially available KRATON G2705 from the Shell Chemical Company.

Another suitable styrene and hydrocarbon copolymer includes the selectively hydrogenated block copolymers of the vinyl aromatic hydrocarbon and the conjugated diene grafted with an alpha, beta-olenfically unsaturated monocarboxylic or dicarboxylic acid reagent. The carboxylic acids include derivatives such as anhydrides, imides, metal salts, and esters. The grafting can be performed by melt or solution mixing of the hydrogenated block copolymer and the carboxylic reagent in the presence of a free radical initiator.

FIG. 1 shows a monolayer medical tubing 10 of the present invention fabricated from the blend of the present invention. The medical tubing 10 is preferably tumble blended and extruded by a high mixing screw with a tight screw pack. The tubing 10 preferably has an inner diameter within the range of 0.08 in. to 0.5 in., more preferably within the range of 0.1 in. to 0.30 in., or any range or combination of ranges therein. The first component of the homopolymer or copolymer of polypropylene must be dispersed in the styrene and hydrocarbon copolymer matrix to insure melt strength for the tubing extrusion. It is believed that a portion of the first component flows to the surface of the tubing so that the medical tubing achieves a glossier surface. With the first component present on the surface of the medical tubing, dust adherence is greatly reduced.

FIG. 1 also shows the medical tubing 10 of the present invention sealed to a CAPD connector 12. Tubing 10 of the present invention exhibits sufficient elastic properties for sealing to polymeric housings. In particular, during steam sterilization, the tubing of the present invention will self-seal or bond mechanically or chemically to housings, couplers 14, and Y-junction connectors 16 produced from a polymeric material without the use of adhesives or solvents. Such polymeric materials include polycarbonates, polyesters, and polypropylenes as well as polyolefin alloys such as those disclosed in commonly assigned patent application Ser. No. 08/153,823.

During an autoclave process, the tubing and the housings are subjected to a sterilizing steam having a temperature of 121° C. and elevated pressures. These conditions are sufficient to melt or soften a portion of the polymeric blend and cause the blend to essentially melt to the housings to form a bond therewith.

Tubings of the present invention have a modulus of elasticity preferably less than 10,000 psi, more preferably within the range 500 to 5,000 psi, or any range or combination of ranges therein. In addition, the medical tubing preferably will meet the following physical property requirements: coil recovery greater than 30%, more preferably greater than 50%, and most preferably greater than 70%, or any range or combination of ranges therein; shrinkage less than 10%, more preferably less than 5%, and most preferably less than 1%, or any range or combination of ranges therein; and, a yield strength preferably less than 50,000 psi, and more preferably within the range of 25,000 to 45,000 psi, or any range or combination of ranges therein.

EXAMPLES

Example 1

Medical tubing was extruded from a Shell Kraton G2705 styrene-ethylene-butene-styrene material. The extruder used was a 1.5 inch standard mixing screw extruder. The medical tubing was extruded at approximately 14 ft/min using open water tank with extrusion temperatures as follows: zone 1 at 370° F., zone 2 at 380° F., zone 3 at 390° F., zone 4 at 400° F., and the clamp die at 400° F. The coil recovery, spring constant, shrinkage, modulus of elasticity, optical clarity, and capability of high speed productivity are summarized in Table 1.

Example 2

The tubings of Example 2 to Example 5 were extruded at approximately 24 ft/min using a vacuum sizer, and the extruder was maintained at a constant temperature in all zones and dies. A Dutch-weave screen pad was used. A polymeric material was produced from 99% Shell Kraton G2705 and 1t polypropylene (Montell PF611, 30 MFI). Tubing was fabricated using a similar extruder at similar speeds to the procedure used in Example 1. The tubing was produced with a vacuum sizer rather than at open water. At 360° F., the tubing had poor surface appearance. The surface appearance was optimized at 370° F. As the temperature was increased to 375° F. and above, a localized reduction in the diameter dimension of the tubing, or necking, occurred. The surface appearance became glossier as temperature was increased. The tubing's physical properties and optical quality are summarized in Table 1.

Example 3

In Example 3, the composition of the polymeric material was modified to 98% Shell Kraton G2705 and 2% polypropylene (Montell PF611, 30 MFI). Tubing was produced in a manner identical to Example 2. At 360° F., the tubing's exhibited a poor surface appearance. At 375° F. and above, the tubing began to neck. Again, as the temperature was increased, the surface became glossier. Table 1 summarizes the tubing's physical properties and optical quality. A large scale run was performed at 50 ft/min with a double Dutch-weave screen pad. The extrusion temperature window was widened significantly with no necking phenomena observed.

Example 4

In Example 4, the composition of the polymeric material was modified to 95% Shell Kraton G2705 and 5% polypropylene (Montell PF611, 30 MFI). Tubing was produced in a manner identical to Example 2. At 390° F. the tubing's surface appearance was glossy as desired. At 395° F., the tubing began to neck. Again, as the temperature was increases, the surface became glossier. Table 1 summarizes the results of Example 4.

Example 5

In Example 5, the amount of polypropylene added to the polymeric material was increased to 10%; the balance of the polymeric material was Shell Kraton G2705. No necking was observed at extrusion temperatures as high as 420° F. Again, Table 1 summarizes the results of this trial.

TABLE 1

EXAMPLES

| Composition | Coil Recovery (%) | Coil Spring Constant (lb/in) | Shrinkage (%) | Modulus of Elasticity (psi) | Post-Autoclave Clarity | Capability of High Speed Productivity (>50 ft/m in) |
|---|---|---|---|---|---|---|
| Shell Kraton G2705 | 76 | 0.29 | 3 | 740 ± 160 | Opaque | Poor |
| 1% Polypropylene (Montell PF611, 30 MFI) 99% Kraton G2705 | 69 | 0.37 | 1 | 1042 ± 79 | Translucent | Poor Dimension Stability |
| 2% Polypropylene (Montell PF611, 30 MFI) 98% Kraton G2705 | 63 | 0.35 | 1 | 1164 ± 41 | Translucent | Yes |
| 5% Polypropylene (Montell PF611, 30 MFI) 95% Kraton G2705 | 50 | 0.59 | 0 | 2413 ± 165 | Translucent | Yes |
| 10% Polypropylene (Montell PF611, 30 MFI) 90% Kraton G2705 | 42 | 0.74 | 0 | 2810 ± 551 | Translucent | Yes |
| 2% Polypropylene (Exxon PP, 800 MFI) 98% Kraton G2705 | 59 | — | 1 | 1164 ± 41 | — | Sizing Difficulty |
| 7% Polypropylene (Montell PF611, 30 MFI) 75% Kraton G2705, 25% Kraton G1652 (FILM SAMPLE) | N/A | N/A | N/A | 1500 | Translucent | N/A |

Without the addition of polypropylene to the oil-modified SEBS, the material was difficult to extrude at a commercially acceptable rate because phase separation and melt fracture occurred. This resulted in tubing that would break into pieces as it was being extruded. The addition of up to 10% by weight polypropylene to the oil-modified SEES increased the melt strength and melt flow index of the polymeric material so that a suitable monolayer, autoclavable, low modulus, medical tubing could be produced at a commercially acceptable rate.

While specific embodiments have been illustrated and described, numerous modifications are possible without departing from the spirit of the invention, and the scope of protection is only limited by the scope of the accompanying claims.

We claim:

1. A steam sterilizable monolayer medical tubing consisting essentially of:
   a blend of a melt strength enhancing agent including from 1 to 10% by weight of a homopolymer or copolymer of polypropylene having free-end long chain branches of propylene units and a melt flow index of greater than 10 grams/10 min., and 90–99% by weight of a second component selected from the group consisting of (i) a selectively hydrogenated block copolymer of a vinyl aromatic hydrocarbon and a conjugated diene and (ii) a selectively hydrogenated block copolymer of a vinyl aromatic hydrocarbon and a conjugated diene to which has been grafted, an alpha, beta-olenfically unsaturated monocarboxylic or dicarboxylic acid reagent.

2. The tubing of claim 1 wherein the second component is an styrene-ethylene-butene-styrene block copolymer.

3. The tubing of claim 2 wherein the styrene-ethylene-butene-styrene block copolymer is modified with 5–40% by weight of an oil.

4. The tubing of claim 1 wherein the second component is an oil-modified styrene-ethylene-butene-styrene block copolymer comprising 5–40% oil.

5. The tubing of claim 1 wherein the melt strength enhancing agent has a melt flow index of at least 30 grams/10 min.

6. The tubing of claim 1 wherein the tubing has the following physical characteristics:
   a coil recovery is at least 30;
   a modulus of elasticity from about 400 psi to 10,000 psi; and,
   a yield strength less than 50,000 psi.

7. The tubing of claim 1 wherein the tubing has a modulus of elasticity less than 3,500 psi.

8. The tubing of claim 1 wherein the homopolymer or copolymer of polypropylene is high melt strength modified.

9. The tubing of claim 1 wherein the tubing has a translucent post-autoclave clarity.

* * * * *

UNITED STATES PATENT AND TRADEMARK OFFICE
CERTIFICATE OF CORRECTION

PATENT NO.   : 6,303,200 B1
DATED        : October 16, 2001
INVENTOR(S)  : Lecon Woo et al.

It is certified that error appears in the above-identified patent and that said Letters Patent is hereby corrected as shown below:

Column 3,
Line 61, delete "10by" and insert -- 10% by --

Column 5,
Lines 5 and 6, delete "SEES" and insert -- SEBS --

Column 6,
Line 25, delete "1t" and insert -- 1% --

Column 7,
Line 28, delete "10" before "addition".
Line 29, delete "SEES" and insert -- SEBS --

Signed and Sealed this

Twenty-sixth Day of March, 2002

Attest:

JAMES E. ROGAN
Attesting Officer      Director of the United States Patent and Trademark Office